United States Patent [19]

Chen

[11] Patent Number: 5,858,644
[45] Date of Patent: Jan. 12, 1999

[54] ANALYSIS OF ANALYTES IN BIOLOGICAL FLUIDS

[75] Inventor: Fu-Tai Albert Chen, Brea, Calif.

[73] Assignee: Beckman Instruments, Inc., Fullerton, Calif.

[21] Appl. No.: 452,831

[22] Filed: May 30, 1995

Related U.S. Application Data

[63] Continuation of Ser. No. 226,930, Apr. 13, 1994, abandoned.

[51] Int. Cl.$^6$ .............................. C12Q 1/00; G01N 33/48
[52] U.S. Cl. .................................. 435/4; 435/25; 435/26; 435/39; 435/190; 436/12; 436/63; 436/516; 204/450; 204/451; 204/452
[58] Field of Search .................................. 435/4, 25, 26, 435/39, 190; 436/12, 63, 516; 204/450, 451, 452

[56] References Cited

U.S. PATENT DOCUMENTS

| | | | |
|---|---|---|---|
| 4,927,265 | 5/1990 | Brownlee | 356/73 |
| 5,120,413 | 6/1992 | Chen et al. | 204/180 |
| 5,139,630 | 8/1992 | Chen | 204/180.1 |
| 5,145,567 | 9/1992 | Hsieh et al. | 204/180.1 |
| 5,202,006 | 4/1993 | Chen | 204/180.1 |
| 5,228,960 | 7/1993 | Liu et al. | 204/182.8 |
| 5,234,586 | 8/1993 | Afeyan et al. | 210/198.2 |
| 5,296,115 | 3/1994 | Rocklin et al. | 204/180.1 |
| 5,310,462 | 5/1994 | Chen | 204/180.1 |

FOREIGN PATENT DOCUMENTS

| | | |
|---|---|---|
| WO8504256 | 9/1985 | WIPO. |
| WO9217259 | 10/1992 | WIPO. |

OTHER PUBLICATIONS

Merlini, G. et al., "Identification of Specific Plasma Proteins Determining the Agarose Gel Electrophoresis by Immunosubtraction Technique", *The Journal of Clinical Chemistry and Clinical Biochemistry*, vol. 21, No. 12, 1983, pp. 841–844.

English translation of Abstract of Japanese Patent Publication No. A–5 087 813, filed Apr. 15, 1991 by Fuji Pharmaceutical and published Apr. 6, 1993.

English translation of Abstract of Japanese Patent Publication No. A–612 80570, filed Jun. 6, 1985 by K. Hirobashi and published Dec. 11, 1986.

Avila et al, *J. Org. Chem.*, vol. 58, No. 20, pp. 5508–5512, 1993.

Chen et al, *Clin. Chem.*, vol. 37, No. 1, pp. 14–19, 1991.

Chen et al, *Electrophoresis*, vol. 15, pp. 13–21, 1994.

*Primary Examiner*—Cecilia J. Tsang
*Assistant Examiner*—Abdel A. Mohamed
*Attorney, Agent, or Firm*—William H. May; Gary T. Hampson; David A. Farah

[57] ABSTRACT

A method for detecting an analyte in a sample uses both the specificity of an enzymatic reaction and the separation power of capillary electrophoresis. In general, the method comprises: (1) subjecting a first aliquot of the sample to an analytical technique such as capillary electrophoresis, which generates a first output such as an electropherogram; (2) reacting a second aliquot of the sample in an enzyme-catalyzed reaction converting the analyte into a product, the product being detectable by the analytical technique; (3) subjecting the second aliquot to the analytical technique to generate a second output; (4) in the case of electrophoresis, measuring the absorbance of the first and second outputs (electropherograms) as a function of migration distance along the electropherogram at at least one wavelength at which either the analyte or the product absorbs to produce a first absorbance scan and a second absorbance scan; and (5) comparing the first absorbance scan with the second absorbance scan to detect the analyte. The reaction can involve a coenzyme and the analytical technique can be directed to the coenzyme. Alternatively, at least two enzymes can be used, the first enzyme generating a first product that is then acted upon by the second enzyme.

3 Claims, 4 Drawing Sheets

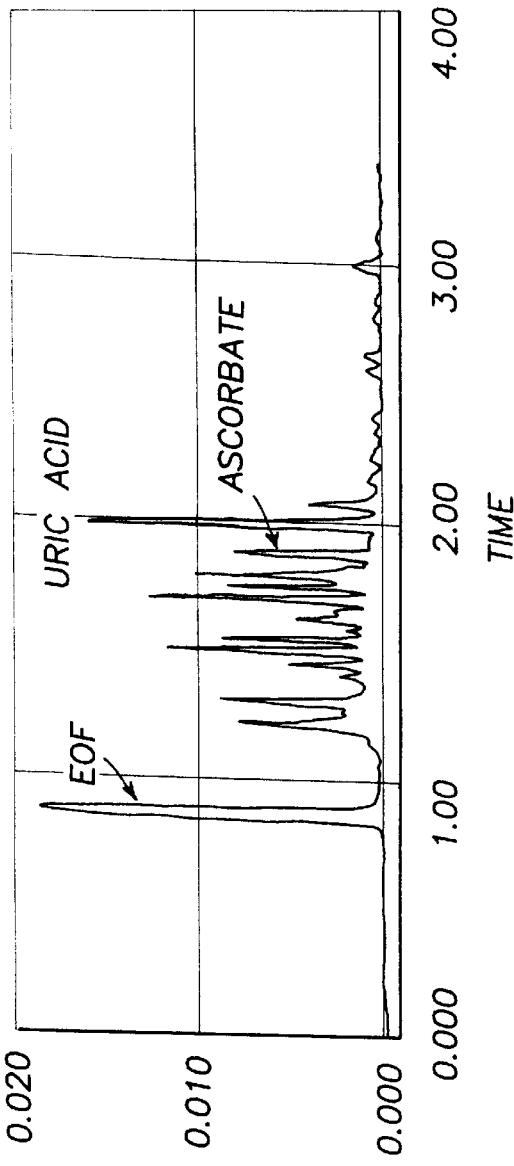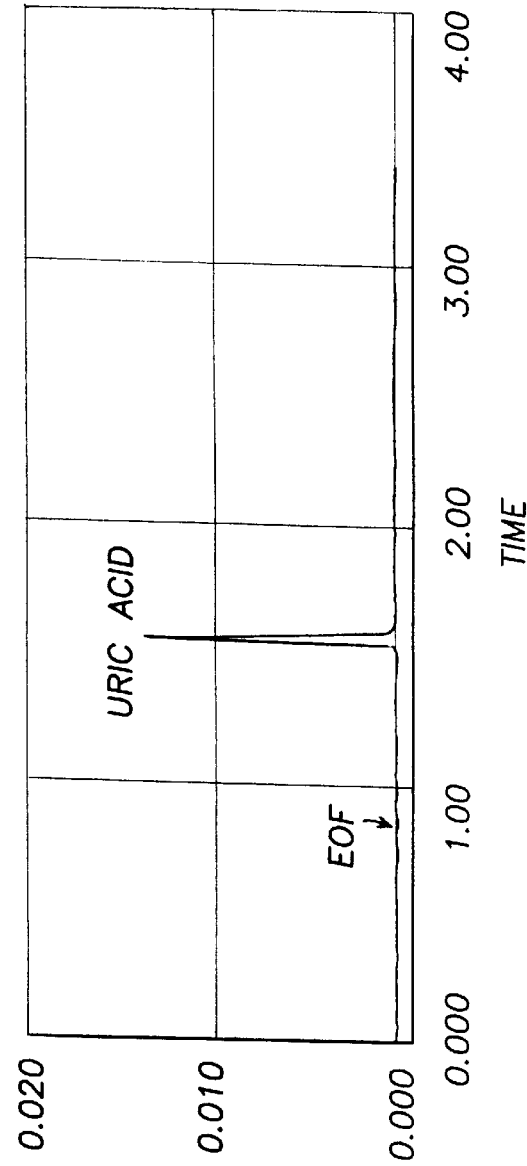

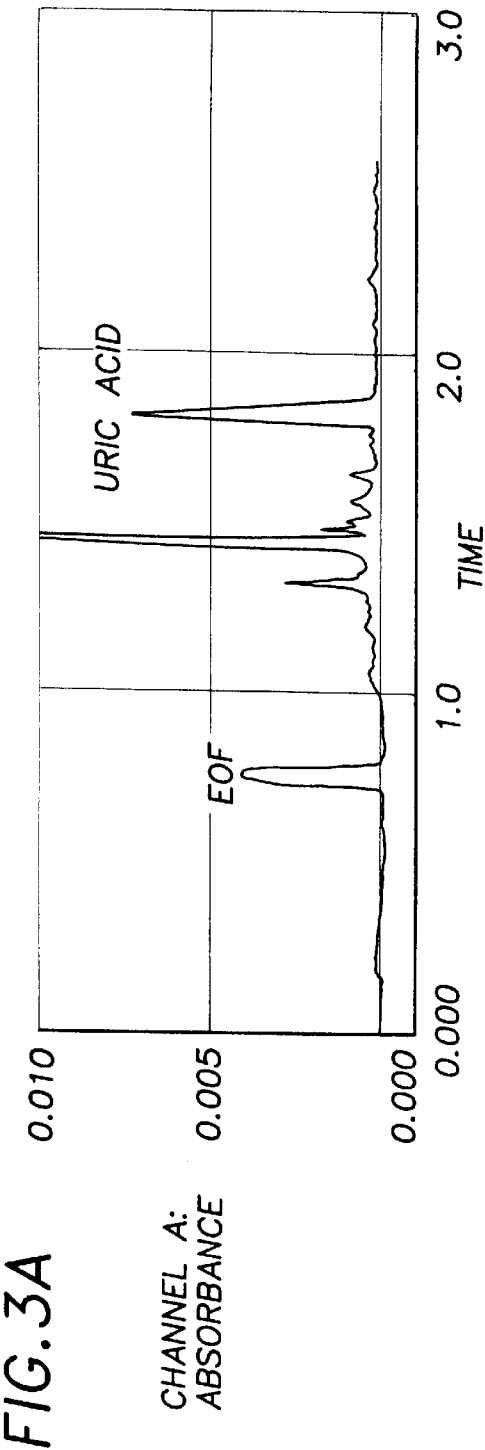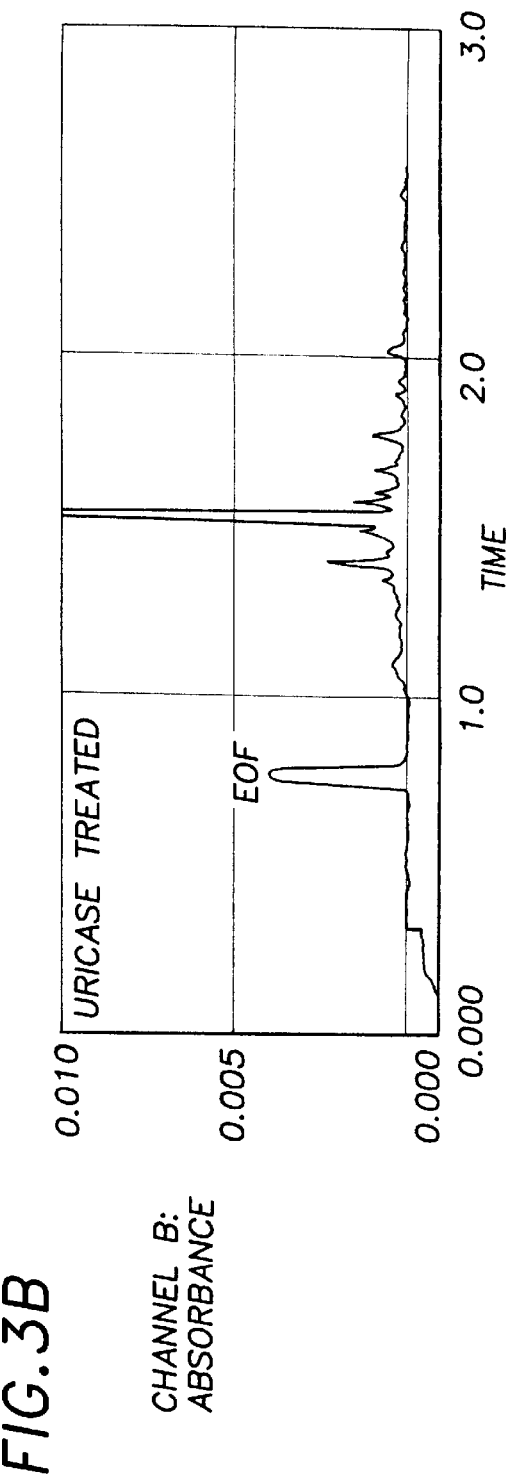

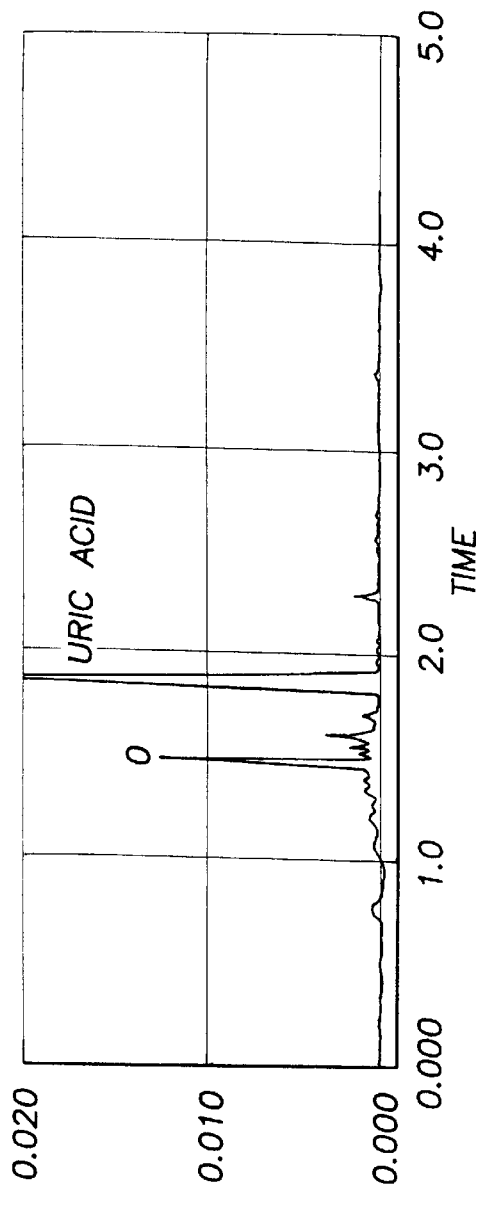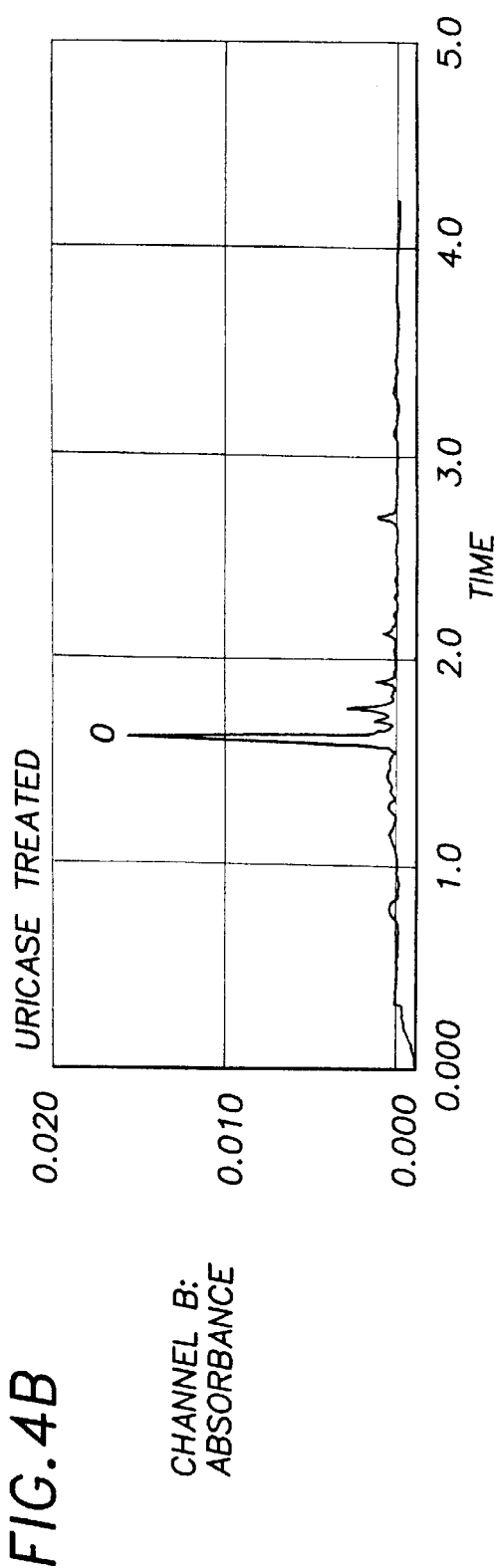

ANALYSIS OF ANALYTES IN BIOLOGICAL FLUIDS

This is a continuation of application Ser. No. 08/226,930 filed on Apr. 13, 1994, now abandoned.

BACKGROUND

This invention is directed to methods for detecting analytes in biological fluids, typically using a combination of capillary electrophoresis and an enzymatic reaction.

For many purposes, it is important to detect analytes in biological fluids such as urine, plasma, lymphatic fluid, or cerebrospinal fluid. In many cases, particular analytes are markers of disease conditions, and the disease condition is detected either by the presence of an otherwise abnormal analyte or the presence of an abnormal concentration of an otherwise normally occurring analyte. For example, the amino acid phenylalanine is present in abnormally high concentrations in the serum of individuals with the genetic disorder phenylketonuria, which can cause severe mental retardation in untreated individuals. Thus, accurate diagnosis of this genetic disorder is essential. Other aminoacidurias are also inheritable genetic disorders and can result in a wide variety of serious consequences. These disorders are treated by special diets, and it is therefore essential that the presence of the disease be diagnosed accurately.

Another example of an analyte that is frequently assayed for clinical purposes is uric acid. Uric acid is a breakdown product of purines, and is a normal constituent of serum and urine. However, higher than normal concentrations of uric acid in serum are characteristic of gout, which can cause arthritis and renal disease. Other syndromes, such as Lesch-Nyhan Syndrome, are also associated with higher than normal uric acid levels. This syndrome is characterized by the deficiency of hypoxanthine-guanine phosphoribosyl-transferase and is manifested clinically by mental retardation, abnormal muscle movements, and behavioral problems such as self-mutilation and aggressiveness.

Many other analytes are also assayed to monitor the development and treatment of many clinical conditions. However, the assay of such analytes in complex biological fluids is difficult. In many cases, it is difficult to identify many of the substances present in these fluids, even with a sensitive separation technique such as capillary electrophoresis. For example, separation of urine by capillary electrophoresis results in more than fifty readily recognizable peaks, and only a minority of these peaks have so far been identified. Because of the presence of components in urine such as proteins and salts, the migration time of each species present can be affected drastically when compared to an electropherogram of a pure sample of the substance.

The difficulty of identifying such analytes is even greater in serum, because the protein concentration in serum is approximately three orders of magnitude greater than it is in urine, which causes a substantially greater degree of interference and masking.

Therefore, there is a need for an analytical method that detects analytes in complex biological fluids such as serum and urine, and that overcomes the interference introduced by salts and proteins. Such a method should be able to identify and quantitate a wide variety of analytes and do so specifically, avoiding cross reactions. The method should also be able to distinguish between compounds of similar structure such as the amino acids aspartate and glutamate, or steroids with the same ring structure and different substituents. Furthermore, the method should be easy to carry out, give rapid results, and use relatively small samples compatible with current clinical practice.

SUMMARY

I have developed a method for detecting an analyte in a sample that meets these needs. In the method, a first aliquot of a sample is analyzed with a selected analytical technique, typically capillary electrophoresis, to generate a first output that includes a first signal representative of the analyte content of the sample. A second aliquot of the sample is reacted in a reaction that reduces the analyte content of the second aliquot. Typically, this is an enzymatically catalyzed reaction that produces a product separable by the analytical technique from the analyte. The reacted second aliquot is then analyzed with the selected analytical technique to generate a second output. The second output includes substantially no signal representative of the analyte when the reacted second aliquot contains no analyte. Alternatively, the second output has a second signal representative of the analyte content of the reacted second aliquot with the second aliquot contain some of the original analyte, wherein the second output is less than the first output. Then the two outputs are compared to determine the presence of the analyte in the sample.

For example, when the analytical technique is capillary electrophoresis, the analysis steps includes producing first and second absorbance scans as the first and second outputs, respectively, wherein an absorbance peak representing the analyte is in the first scan, but the corresponding absorbance peak is missing or greatly reduced in the second scan. The absorbance peaks are the signals representative of the analyte. Comparing the two absorbance peaks reveals which absorbance peak of the first scan is missing or reduced in the second scan, thereby "unmasking" the absorbance peak of the analyte, so that the analyte content of the sample can be determined.

When capillary electrophoresis is used as the analytical technique, a first electropherogram is generated from the first aliquot and a second electropherogram is generated from the second aliquot. The absorbances of the first and second electropherogram are measured as a function of the migration distance along the electropherogram at at least one wavelength, at which either the analyte or the product absorbs to produce the first and second absorbance scans. The wavelength can be a wavelength at which the analyte substantially absorbs light. In this case, the absorbance peak is not present, or is greatly reduced, in the electropherogram of second aliquot. Alternatively, the wavelength can be one at which only the product substantially absorbs light. In this case, the absorbance peak of the product, but not the analyte, is present in the electropherogram from the reacted second aliquot.

The step of reacting preferably utilizes a specific enzyme-catalyzed reaction. Depending on the analyte, the enzyme can be selected from the group consisting of uricase, alcohol dehydrogenase, L-glutamate dehydrogenase, 3-α-hydroxysteroid dehydrogenase, hexokinase, glucose oxidase, β-glucuronidase, lactate dehydrogenase, oxalate oxidase, amino acid decarboxylase, arginase, arginine deiminase, tyrosinase, phenylalanine-4-monooxygenase, tryptophan oxygenase, or proline oxidase.

In a preferred embodiment of the invention, for the detection of urea as the analyte, the enzyme is uricase. Preferred wavelengths for producing an electropherogram in this preferred embodiment include, but are not limited to, 200 nm and 280 nm.

In another embodiment of the invention, the reaction for the second aliquots can be an enzyme-catalyzed reaction that requires a coenzyme and the utilization of the coenzyme can be measured. In this version of the invention, coenzyme is added to both the first and second aliquot, but the enzyme is added only to the second aliquot. Both aliquots are subjected to the selected analytical technique to generate the first and second outputs. The first output includes a signal representative of the coenzyme content of the sample. The second output has a reduced signal (or no signal) representative of the coenzyme content of the reacted second aliquot, because the coenzyme is consumed in the enzyme-catalyzed reaction in the second aliquot. By comparing the outputs of the first aliquot and the reacted second aliquot, the decrease in the concentration of a coenzyme in the second aliquot caused by the conversion of the analyte to the product in the enzymatic reaction can be determined, thus providing an indication that the analyte is present in the sample.

The coenzyme can be any of the oxidized and reduced forms of nicotinamide adenine dinucleotide, the oxidized and reduced forms of nicotinamide adenine dinucleotide phosphate, the oxidized and reduced forms of flavin adenine dinucleotide, adenosine triphosphate, or guanosine triphosphate.

It is important in the present invention that the analytical technique be selected and an appropriate reaction be used so that the analytical technique can distinguish between the analyte and the product produced in the reaction step. To achieve this result, it may be necessary to subject the product produced in the reaction of the second aliquot to a further reaction, in order to produce a second product that is distinguishable from the analyte by the analytical technique. This second reaction can be an enzyme-catalyzed reaction.

BRIEF DESCRIPTION OF THE DRAWINGS

These and other features, aspects, and advantages of the present invention will become better understood with reference to the following description, appended claims, and the accompanying drawings where:

FIG. 1A is a capillary electropherogram of a urine sample showing the presence of uric acid and ascorbate;

FIG. 1B is a capillary electropherogram of a pure sample of uric acid;

FIG. 3A is another capillary electropherogram at 200 nm of a urine sample, showing the presence of uric acid;

FIG. 3B is a capillary electropherogram of the urine sample of FIG. 3A subsequent to treatment with uricase, showing almost complete disappearance of the uric acid peak;

FIG. 4A is another capillary electropherogram at 280 nm of a urine sample, again showing the presence of uric acid; and FIG. 4B is a capillary electropherogram of the urine sample of FIG. 4A subsequent to treatment with uricase, again showing an almost complete disappearance of the uric acid peak.

DESCRIPTION

Figure 2A:
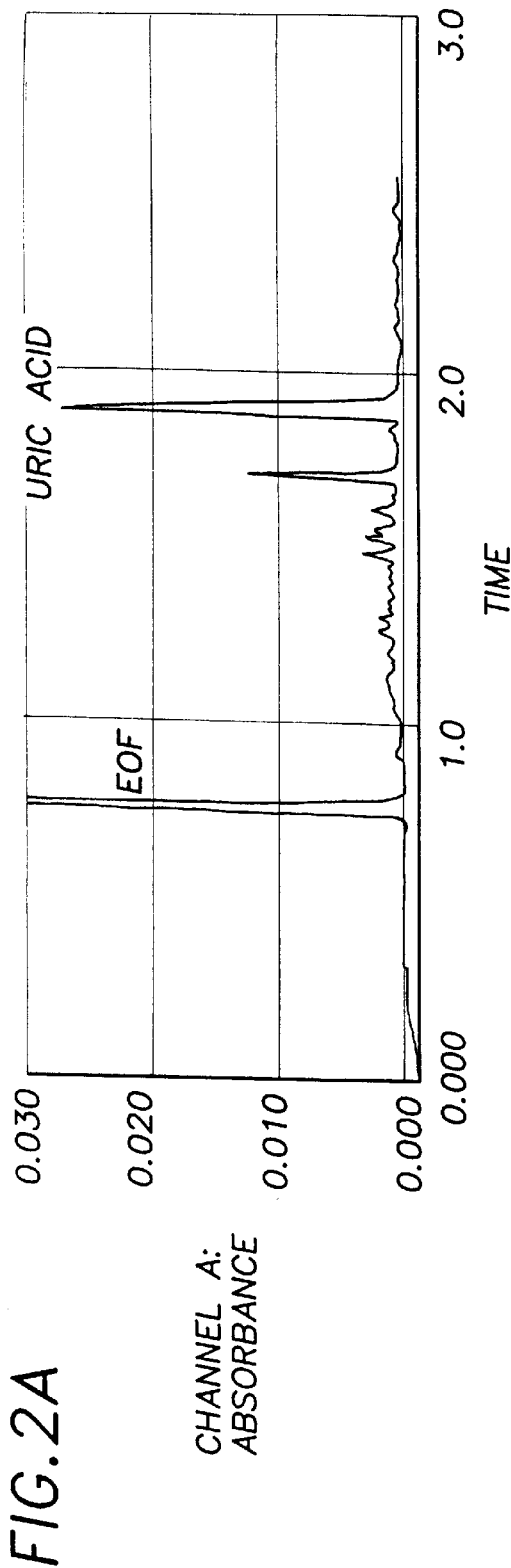
FIG. 2A is another capillary electropherogram of a urine sample, showing the presence of uric acid.

I have developed a method for quantitating an analyte in a complex mixture such as serum or urine by using the specificity of a selected reaction, preferably an enzymatic reaction, and the specificity of a selected analytical technique, preferably capillary electrophoresis.

In a preferred version of the invention, the method is based on the ability of capillary electrophoresis to separate and identify single molecules out of complex mixtures. The molecule identified can either be the analyte, a product of one or more reactions catalyzed by an enzyme that catalyzes a reaction involving the analyte, or another reagent involved in one or more such reactions, such as a coenzyme. The identification is made by noting the difference in the capillary electrophoresis electropherogram for an aliquot of the sample in which the enzymatic reaction has not taken place as compared to a second aliquot in which the enzymatic reaction or reactions have occurred.

The invention is not limited to use of capillary electrophoresis as the analytical technique. Among other analytical techniques that can be used are conventional electrophoresis and chromotographic separation. Further, the reaction need not necessarily be enzyme-catalyzed. For example, where ascorbate is the analyte, a chemical oxidation technique can be used for effecting the reaction.

However, due to the specificity of the capillary electrophoresis and the specificity of enzyme-catalyzed reactions, these are preferred. Thus, the present invention will be described in detail with regard to these specific techniques.

I. METHODS OF CAPILLARY ELECTROPHORESIS ANALYSIS USING ENZYMES

A. Method Involving a Single Enzyme

In one embodiment of the present invention, a single enzyme can be used and the difference in the electropherograms with and without the enzymatic reaction is used to determine the analyte. In general, this method comprises:

(1) subjecting a first aliquot of the sample to capillary electrophoresis to generate a first electropherogram to separate the analyte from other components in the sample;

(2) reacting a second aliquot of the sample in an enzyme catalyzed reaction converting the analyte into a product, the product separable by capillary electrophoresis from the analyte and from other components in the sample;

(3) subjecting the second aliquot to capillary electrophoresis to generate a second electropherogram to separate the product from other components in the sample and from the analyte;

(4) measuring the absorbance of the first and second electropherograms as a function of migration distance along the electropherograms at at least one wavelength at which either the analyte or the product absorbs to produce a first absorbance scan and a second absorbance scan; and (5) comparing the first absorbance scan with the second absorbance scan to detect and/or determine the analyte.

The wavelength used can be a wavelength at which only the analyte substantially absorbs light. In that case, the effect of the enzymatic reaction is to deplete the analyte and cause the disappearance of the peak corresponding to the analyte. Alternatively, the wavelength can be a wavelength at which only the product substantially absorbs light, so that a peak corresponding to the product appears in the electropherogram of the second aliquot and is absent in the first aliquot.

This is done in order to unequivocally identify the analyte, because the migration of the analyte in capillary electrophoresis can be substantially different when the analyte is present in a complex mixture such as serum or urine than when it is present in a pure or substantially pure sample.

Thus, the specificity of the enzyme is used to identify the peak either of the product or of the analyte.

The enzyme can be any enzyme that specifically modifies the analyte, either by degrading it or by converting it to a product of different mobility. Among the enzymes that can be used are hydrolases, phosphorylases, lyases, oxidases, dehydrogenases, methylases, isomerases, and synthetases. Among the enzymes that can be used are uricase, alcohol dehydrogenase, L-glutamate dehydrogenase, 3-α-hydroxysteroid dehydrogenase, hexokinase, glucose oxidase, β-glucuronidase, lactate dehydrogenase, oxalate oxidase, amino acid decarboxylase, arginase, arginine deiminase, tyrosinase, phenylalanine-4-monooxygenase, tryptophan oxygenase, and proline oxidase. The method is not limited to these enzymes.

Exemplary analyte-enzyme-product combinations are listed in Table I, as well as the coenzyme, if any, used.

TABLE I

| ANALYTE | ENZYME | COENZYME | PRODUCT |
|---|---|---|---|
| ascorbic acid | ascorbic oxidase | None | dehydroascorbase |
| creatinine | creatanase | None | creatin |
| glucose | glucose oxidase | None | gluconic acid |
| glucose-6-phosphate | dehydrogenase | NAD (yields NADH) | gluconic acid-6-phosphate |
| uric acid | uricase | None | allantoin |
| ethanol | alcohol dehydrogenase | NAD | NADH |
| 3-α hydroxy-steroid | dehydrogenase | NAD | NADH |
| hexose | Hexokinase | NAD | NADH, hexonic acid |
| actate | lactic dehydrogenase | NAD | pyruvic acid, NADH |
| oxalic acid | oxalate oxidase | | $H_2O_2$ |
| phenylalanine | phenylalanine-4-monooxygenase | | tyrosine |

In one particularly useful application for urine, the analyte is uric acid and the enzyme is uricase.

Another useful application is the detection of phenylalanine in serum to identify phenylketonuria (PKU) using phenylalanine oxidase as the enzyme and phenyl pyruvic acid as the product. Similarly, phenylpyruvic acid can be detected in urine to confirm PKU using decarboxy laser as the enzyme and phenyl acetic acid as the product.

The wavelength used is chosen by knowledge of the ultraviolet or visible absorption spectrum of the analyte or of the product. Typically, the wavelength is between about 200 nanometers and about 400 nanometers, most typically no greater than about 370 nanometers, i.e., in the ultraviolet region of the spectrum. When the analyte is uric acid and the enzyme is uricase, suitable wavelengths for detection of the uric acid are 200 nm and 280 nm. If the analyte is an aromatic compound, an amino acid, or a nucleic acid monomer, suitable wavelengths are readily determined.

The reaction conditions used for the reaction of the second aliquot depends on the analyte and the particular enzyme, and in nearly all cases, are apparent to one of ordinary skill in the art. Typically, the reaction takes place in a suitable buffer to stabilize the pH. Typically, the pH is maintained in a range of from about 5 to about 10, depending on the enzyme. In many cases, the pH used is one closer to neutrality, from about 6 to about 8.5, more typically from about 7 to about 7.5. A large number of suitable buffers exist that can be used in the process of the present invention. Typical buffers include phosphate, acetate, tris (hydroxyamino)methane ("Tris") and a number of buffers such as MES, ADA, PIPES, ACES, BES, MOPS, PES, HEPES, EPPS, TRICINE, BICINE, CHES, and CAPS, described in N. E. Good et al., *Biochemistry* 5:467–477 (1966).

The temperature of the reaction is also chosen according to the behavior of the analyte and the enzyme. Typically, the reaction can be performed at a temperature ranging from about 4° to about 37° C. Typically, the reaction is performed at around room temperature, i.e., from about 20° to about 25° C. However, most enzymatic reactions occur more rapidly at increased temperatures, and thus, it can be desirable to carry out the reaction at an increased temperature.

The reaction mixture can also include other components as required for the activity of the enzyme. As discussed below, many enzymes require coenzymes for activity, and, if necessary, such coenzymes can be included. When included, they are preferably included in a saturating amount to facilitate the enzymatic reaction. In other cases, particular monovalent or divalent cations, such as $Na^+$, $K^+$, $Ca^{2+}$, $Mg^{2+}$, or other ions can be added. For the enzymes that are usable in the present invention, the reaction conditions are well-known in the art.

The quantity of enzyme used is sufficient to convert the analyte to the product. Typically, the analyte is present in the reaction mixture at an initial concentration at least equal to the $K_m$ for the analyte for the particular enzyme used. At this concentration, the rate of the reaction is half-maximal. The period of incubation depends on the analyte concentration and the quantity of enzyme, as well as the turnover number of the enzyme. It typically ranges from about 10 seconds to about 1 hour, more typically from about 1 minute to about 10 minutes. Variations from the above procedures are readily apparent to one of ordinary skill in the art with knowledge of the properties of the particular enzyme and analyte.

B. Use of Coenzyme-Utilizing Enzymes

The reactions catalyzed by many enzymes require the participation of coenzymes. Among the coenzymes that are frequently involved in enzymatic reactions are adenosine triphosphate, guanosine triphosphate, coenzyme A, thiamine diphosphate, pyridoxal phosphate, the oxidized and reduced forms of nicotinamide-adenine dinucleotide, the oxidized and reduced forms of nicotinamide-adenine dinucleotide phosphate, the oxidized and reduced forms of flavin adenine dinucleotide, and the oxidized and reduced forms of riboflavin 5'-phosphate. Other coenzymes are known in the art.

If a reaction catalyzed by an enzyme involves a coenzyme, the change in concentration of the coenzyme as the result of the enzymatic reaction can be used to monitor the extent of the reaction.

In general, where the selected analytical technique is capillary electrophoresis, this method comprises the steps of:

(1) adding a quantity of a coenzyme sufficient to support an enzyme-catalyzed reaction to first and second aliquots of the sample;

(2) subjecting the first aliquot to capillary electrophoresis to generate an electropherogram to separate the analyte and the coenzyme from other components in the sample;

(3) reacting the second aliquot with an enzyme to catalyze the reaction converting the analyte into a product, the reaction requiring the participation of the coenzyme and reducing the coenzyme content of the second aliquot, the coenzyme being converted to a derivative in the reaction, the coenzyme being separable from the analyte and the product by capillary electrophoresis;

(4) subjecting the second aliquot to capillary electrophoresis to generate an electropherogram to separate the coenzyme from the analyte and the product and from other components in the sample;

(5) measuring the absorbance of the first and second electropherograms as a function of migration distance along the electropherogram at at least one wavelength at which the coenzyme absorbs to produce a first absorbance scan and a second absorbance scan; and (6) comparing the first absorbance scan with the second absorbance scan to detect and/or determine the analyte by determining the decrease in the concentration of the coenzyme in the second aliquot caused by the conversion of the analyte to the product by the enzymatic reaction involving the coenzyme.

Alternatively, the wavelength used for measurements can be one at which the unreacted coenzyme absorbs relatively little. In this version of the method, the wavelength used is a wavelength at which the derivative of the coenzyme resulting from the reaction absorbs. This alternative can be used with the interconvertible oxidized and reduced forms of nicotinamide-adenine dinucleotide and nicotinamide-adenine dinucleotide phosphate. For these coenzymes, the reduced form (NADH or NADPH) absorbs significantly at wavelengths such as 334, 340, or 365 nm, where the oxidized forms ($NAD^+$ or $NADP^+$) do not absorb significantly at these wavelengths. Thus, the analyte can be detected and/or determined by determining an increase in the concentration of a derivative of the coenzyme that is the result of the enzymatic reaction. In the case of the $NAD^+$-NADH and $NADP^+$-NADPH interconvertible coenzyme pairs, the derivative is typically the reduced form of the coenzyme resulting from electron transfer from the analyte to the coenzyme as a result of an oxidation-reduction reaction involving the analyte and coenzyme.

C. Coupled Reactions Using Two or More Enzymes

Enzyme reactions can be coupled so that the product of a first enzyme reaction is then used as the substrate for a second enzyme reaction. In some cases, more than two enzymes can be coupled. Examples of coupled enzyme reactions include the following:

(1) the reaction of ATP and 3-phosphoglycerate catalyzed by phosphoglycerokinase to produce ADP and 1,3-diphosphoglycerate, followed by the reaction of the 1,3-diphosphoglycerate with NADH catalyzed by glyceraldehyde phosphate dehydrogenase to produce glyceraldehyde-3-phosphate, $NAD^+$, and inorganic phosphate;

(2) the reaction of cholesterol esters and water with cholesterol esterase to produce cholesterol and free fatty acids, followed by the oxidation of the cholesterol with molecular oxygen catalyzed by cholesterol oxidase to produce cholest-4-en-3-one and hydrogen peroxide, followed by the reaction of the hydrogen peroxide with 4-aminoantipyrine and p-hydroxybenzene sulfonate catalyzed by peroxidase to produce a quinoneimine dye;

(3) the reaction of 2,3-diphosphoglycerate with 2,3-diphosphoglycerate phosphatase in the presence of 2-phosphoglycolic acid to produce 3-phosphoglycerate, and inorganic phosphate, followed by the phosphorylation of the 3-phosphoglycerate with ATP to produce 1,3-diphosphoglycerate and ADP, which is then in turn followed by the reduction of the 1,3-diphosphoglycerate by NADH catalyzed by glyceraldehyde-3-phosphate dehydrogenase to produce glyceraldehyde-3-phosphate and $NAD^+$;and (4) the phosphorylation of glucose with ATP, catalyzed by hexokinase, to produce glucose-6-phosphate and ADP, followed by the oxidation of the glucose-6-phosphate with $NAD^+$ catalyzed by glucose-6-phosphate dehydrogenase to produce 6-phosphogluconate and NADH.

In one version of the invention employing coupled enzymatic reactions, either the analyte or the second product can be assayed after the coupled reaction step. This method comprises the steps of:

(1) subjecting a first aliquot of the sample to an analytical technique, such as capillary electrophoresis, to generate a first output, such as an electropherogram that separates the analyte from other components in the sample;

(2) reacting a second aliquot of the sample in a reaction catalyzed by a first enzyme to convert the analyte into a first product, and reacting the first product in a reaction catalyzed by a second enzyme to convert the first product into a second product, where the selected analytical technique can distinguish between the second product and the analyte;

(3) subjecting the second aliquot to the selected analytical technique, to generate a second output; and (4) comparing the two outputs to determine the presence of analyte or the amount of analyte in the sample.

When the analytical technique is capillary electrophoresis, the outputs are electropherograms, and the comparison can be accomplished by:

(i) measuring the absorbance of the electropherograms as a function of migration distance along the electropherograms at which either the analyte or the second product absorbs to produce respective absorbance scans; and (ii) comparing the absorbance scans to detect and/or determine the analyte.

The absorbance of the first and second electropherograms can be measured at a wavelength at which only the analyte substantially absorbs. In this case what is detected is the disappearance of the analyte in the second aliquot. Alternatively, the absorbance of the first and second electropherograms can be measured at a wavelength at which only the second product substantially absorbs, so that the comparison is made by observing the presence of the second product in the second absorbance scan and its absence from the first absorbance scan.

The "second enzyme" can be only one enzyme, or, as described above, can consist of two or more enzymes. In the latter case, the "second product" is the result of the catalytic action of the last enzyme in the coupled set of reactions.

Alternatively, the second enzyme can be an enzyme that catalyzes a reaction requiring the participation of a coenzyme. In this case, the absorbance of the first and second electropherograms is measured as a function of migration distance along the electropherograms at at least one wavelength at which the coenzyme absorbs to produce a first absorbance scan and a second absorbance scan, and the first absorbance scan is compared with the second absorbance scan to detect and/or determine the analyte by comparing the concentration of coenzyme in the first and second electropherograms. In this method, the second enzymatic reaction is often an enzymatic reaction that involves an oxidation-reduction reaction and results in the generation or utilization of a coenzyme such as $NAD^+$, NADH, $NADP^+$, or $NADP^+$.

II. CAPILLARY ELECTROPHORESIS

Capillary zone electrophoresis (CZE) or capillary electrophoresis, is a technique that employs narrow-bore (10–200 μm inside diameter) capillaries to perform high efficiency separations of both large and small molecules. This separation is facilitated by the use of high voltages, typically 1000 to 30,000 volts, which can generate electro-endoosmotic and electrophoretic flow of buffer solutions and ionic species, respectively, within the capillary. The properties of the separation and the ensuing electropherogram have characteristics resembling a cross between traditional polyacrylamide gel electrophoresis (PAGE) and modern high performance liquid chromatography (HPLC).

The force for moving fluid between the sample input and the sample output of the capillary tube is provided by establishing an appropriate voltage between the sample input and the sample output, generating electrophoretic and electroendoosmotic forces as discussed above.

Electroosmosis is a consequence of the surface charge on the wall of the capillary. The fused silica capillaries that are typically used for separations have ionizable silanol groups in contact with the buffer contained within the capillary. The pI of fused silica is about 1.5. The degree of ionization is controlled mainly by the pH of the buffer. Most buffers in which the pH is greater than 1.5 can ionize the capillary wall. The negatively-charged wall attracts positively charged ions from the buffer, creating an electrical double layer. When a voltage is applied across the capillary, cations in the diffuse portion of the double layer migrate in the direction of the cathode carrying water with them. The result is a net flow of buffer solution in the direction of the negative electrode. In the meantime, the negatively charged analytes, such as proteins, peptides, ionized small molecules, or other species, in the buffer solution can move against the EOF by electrophoretic migration towards the positive electrodes. Despite the electrophoretic migration of the analytes towards the positive electrode (anode), the buffer overwhelms the electrophoretic migration of the analytes, and the analytes migrate toward the negative electrode (cathode). Electrophoretic migration is dependent upon the charge-mass ratio of each molecule, e.g., protein or small molecule, to be separated. Each molecule possesses a specific charge-mass ratio depending upon its size and amino acid composition and thus migrates with a different speed. In the capillary electrophoresis apparatus, the detection window is arranged in relationship to the point at which the sample enters the electrophoretic field so that the sample is carried to the detection window by the buffer. Accordingly, the faster the movement against the buffer, the slower a particular molecule passes the detection window. This is analogous to a group of very lazy rowboaters who are rowing against the current but are carried downstream faster than they can row. An observer at a point some distance downstream would first be reached by the rower who is rowing the slowest, because his net motion would be the closest to that of the current. The rower who was rowing the most vigorously would in fact arrive last at the observer. Thus, proteins with a high degree of negative charge caused by a high proportion of the negatively charged amino acid residues aspartate and glutamate would arrive at the detection window most slowly. Similarly, small molecules with a larger number of negatively charged substituents such as carboxylate and phosphate would arrive at the detection window more slowly than similar molecules with fewer charged groups. Accordingly, what is measured in capillary electrophoresis is the absorption of the sample passing the detection window as a function of time.

The process of capillary electrophoresis can be performed in any apparatus in which the suitable electrophoretic forces can be generated and in which the peaks resulting can be detected. Typically, the capillary electrophoresis system involves a quartz or fused silica capillary tube of circular cross-section and cylindrical outline, equipped with an ultraviolet emitter and monochromator to select the desired wavelength, as well as a photodetector to detect the ultraviolet light that has passed through the sample. Typical dimensions of the capillary tube are 25 μm inner diameter× 27 cm total length. A suitable capillary tube is produced by Polymicro Technologies, Phoenix, Ariz. The outer surface of the capillary can be coated with polyimide to protect the capillary from breakage. The optics module and detector can include a UV light source (deuterium lamp) and a filter in a rotating wheel that passes light of the appropriate wavelength (e.g., 254 nm or 280 nm), as well as a detector that aligns with the aperture of the window. The window can be located at 6.5 cm from the tube outlet. A suitable apparatus for detection of uric acid based on ultraviolet absorbance at 254 nm or 280 nm is the Beckman Instruments P/ACE 2000 CE system (Beckman Instruments, Fullerton, Calif.). This system is computer-controlled and can be used with suitable software, such as the CCE software, and an IBM-compatible personal computer such as an IBM PS/2. Other suitable capillary electrophoresis apparatus can also be used.

Although the detected signal has been described for particular wavelengths, in particular 254 nanometers or 280 nanometers for uric acid detection, it is apparent that the electrophoresis system could operate at many different wavelengths. Signals at multiple discrete wavelengths can be applied to one or more detection paths applied to the tube. Such ranges of wavelengths can be limited or extensive in the electromagnetic spectrum, as long as the masking constituting the window widths suitably excludes the signal at the selected wavelengths from passing through undesirable sections of the tube wall.

Although the electrophoresis system used for the methods of the present invention has been described with reference to a single capillary electrophoresis unit, it is clear that multiple systems can be used in series or tandem to provide for a continuous monitoring process, such as a time series of uric acid concentration in a sample. This may be useful when monitoring the development of clinical conditions such as the response to dietary changes in gout or the response to uricosuric medication.

In other situations, it is possible to have multiple input windows and output windows arranged angularly around the central axis of a capillary tube at selective angles. In different situations, input light of different selected wavelengths can be input into the capillary tube through selected input windows about the axis. Different output windows would then receive the light with the pertinent information about the sample in the tube. This arrangement could, for example, be used to measure both the protein and nucleic acid concentration in a sample relative to two or more internal standards.

III. ANALYTES DETECTABLE BY METHOD OF THE PRESENT INVENTION

A large range of analytes can be assayed by methods of the present invention. These analytes can include any analyte for which a reaction involving that analyte is available. In some cases, absolute specificity for the particular analyte is not required, as long as other potentially reacting analytes are not likely to be present in the sample or can be detected by other methods. The analytes that can be detected by methods of the present invention include sugars, sugar derivatives, nucleotides and derivatives of nucleic acid bases such as uric acid and other purines and pyrimidines, amino acids, amino acid derivatives, steroids, and drugs that are subject to metabolic modification such as hydroxylation, phosphorylation, hydrolysis, conjugation to sugars, cleavage, or oxidation. Typical analytes are identified in Table I.

The invention is illustrated by the following Examples. The Examples are for illustrative purposes only and are not intended to limit the invention.

EXAMPLES

Example 1

Identification of Uric Acid in Urine by Capillary Electrophoresis

Uric acid was identified in urine by the action of the enzyme uricase coupled with capillary electrophoresis.

An aliquot of urine (100 $\mu$l) was subjected to capillary electrophoresis. To identify uric acid, a known quantity of uric acid (0.01 mg) was added to the urine. Capillary electrophoresis was performed on a Beckman P/ACE 2000 series electrophoresis apparatus, which was used with Beckman CCE software, a modification of "System Gold," which was controlled by an IBM PS/2 PC. Dimethyl formamide was used as a marker for flow rate, and is labelled "EOF" in the Figures. Electrophoreses were performed in an untreated fused silica capillary tube with dimensions of 21 $\mu$m diameter×25 cm length. The outer surface of the capillary was coated with polyimide to protect the capillary from breakage (Polymicro Technologies, Inc., Phoenix, Ariz.). The optics module and detector included a UV light source, and a monochromator in a rotating wheel that could be set to either 254 or 280 nanometers, as well as a detector that align with the aperture of the window. The window was located at 6.5 cm from the tube outlet. For capillary electrophoresis, a running buffer was prepared as follows: 9.27 g of boric acid was weighed out and dissolved into 1800 ml of deionized water. A pH meter was calibrated with two standard pH solutions at Ph 7.0 and 10.0, and the boric acid solution was then adjusted to a pH of 10.0 with 1 N NaOH. The boric acid solution was then adjusted to a final volume of 1000 ml using volumetric apparatus and filtered through a 0.22 $\mu$m membrane (Corning, N.Y., Filter Catalogue No. 25952) and stored at room temperature in a glass bottle. The sample diluent was Beckman Instruments ICS diluent, containing 75 mM sodium chloride, 20 mM potassium phosphate, pH 7.0.

The sample was diluted to a final total volume of 100$\mu$l with 1 part of urine or uric acid solution being diluted with 9 parts of sample diluent. The vial was then placed on the sample tray of the electrophoresis apparatus. The parameters for electrophoresis were set as follows: The wavelength for measurements was 200 nm unless otherwise indicated. The temperature was 24° C. The injection mode was pressure injection for 10 seconds.

The operating sequence was set as follows: The column was rinsed with running buffer for 1.5 minutes. The column was then equilibrated with running buffer for 0.5 minutes. Pressure injection was performed for 10 seconds as indicated, and the separation was performed at 20 kilovolts voltage for seven minutes. The column was then rinsed with rinse solution A for 1 minute, and then with rinse solution B for 1 minute. The rinse solution A was 1 N NaOH. The rinse solution B was deionized water.

Column maintenance was as follows: At the beginning of each day, the column was rinsed with rinse solution A for one 1, rinse solution B for 5 minutes, and running buffer for 15 minutes. At the end of each day, the column was rinsed with rinse solution A for 1 minute and rinse solution B for 5 minutes.

FIG. 1A shows the results of electrophoresis of urine. FIG. 1B shows the electrophoresis of 100 $\mu$g/mL of pure uric acid. Quantitation of uric acid in the urine sample (FIG. 1A) by capillary electrophoresis gave a result for uric acid content of 13.4 mg/dl. The presence of ascorbic acid was evident by coinjection of an authentic sample of ascorbate. Uric acid in the urine was determined to be 6.7 mg/dl using uricase coupled with the Trinder reaction (Beckman Uric Acid Trinder Reaction), which involves reaction of the hydrogen peroxide resulting from the action of uricase with 3, 5-dichloro-2-hydroxybenzene sulfonate and 4-aminoantipyrine. The discrepancy was probably due to the interference of ascorbate on the Trinder reaction. Treatment of the urine sample with ascorbate oxidase resulted in an increase of the measured uric acid concentration by the Trinder Reaction to 12.9 mg/dl.

Example 2

Figure 2B:
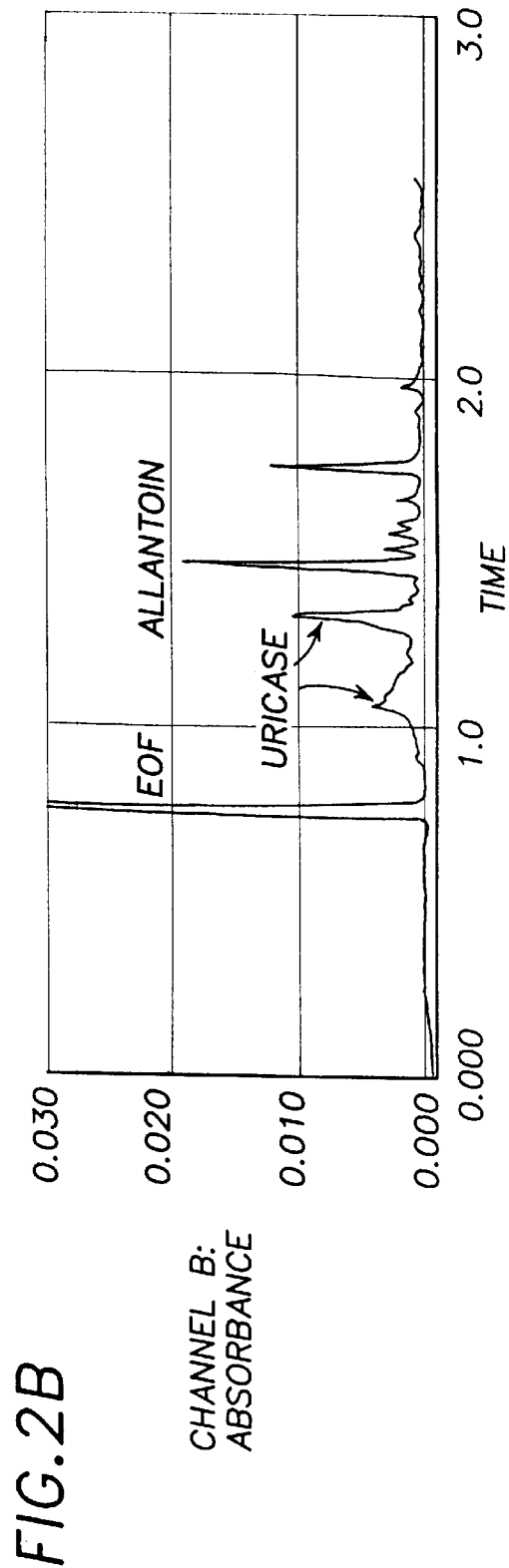
FIG. 2B is a capillary electropherogram of the urine sample of FIG. 2A subsequent to treatment with the enzyme uricase, showing a decrease in the uric acid peak and its replacement with allantoin.

Identification of Uric Acid in Urine Using Capillary Electrophoresis and Enzymatic Reaction In experiments for which the results are shown in FIGS. 2–4, capillary electrophoresis was combined with the use of the enzyme uricase to identify uric acid. In FIG. 2A, the electropherogram of normal urine (200 $\mu$l) is shown prior to uricase treatment. After the addition of 5 $\mu$l uricase (500 $\mu$ml), uric acid was decreased and there was a corresponding increase in the compound allantoin, the product of uricase action on uric acid (FIG. 2B). Detection in FIGS. 2A and 2B was at 200 nm.

Similar results are shown in FIGS. 3A and 3B at for detection at 200 nm and in FIGS. 4A and 4B for detection at 280 nm. In FIGS. 3A and 4A, the urine was electrophoresed without uricase treatment, while in FIGS. 3B and 4B, the urine was electrophoresed subsequent to uricase treatment. In both FIGS. 3B and 4B, the uric acid peak is substantially eliminated after uricase treatment.

ADVANTAGES OF THE INVENTION

The present invention has many advantages. For example, it can be used to determine a wide range of analytes of biological significance. The method can overcome interference by salts, small molecules, or proteins that can alter detection outputs as compared with electrophoresis of pure samples. The method of the present invention can detect clinically important analytes in urine and serum such as phenylalanine, phenylpyruvic acid, and uric acid. The method is rapid, easy to carry out, reproducible, and requires only small sample volumes.

Although the present invention has been described in considerable detail with regard to certain preferred versions thereof, other versions are possible. Therefore, the spirit and scope of the appended claims should not be limited to the descriptions of the preferred versions contained herein.

What is claimed is:

1. A method for detecting an analyte in a sample, the method being suitable for samples containing compounds that can interfere with the detection of the analyte, the method consisting essentially of the following steps:
   (a) analyzing a first aliquot of a sample containing an analyte with a selected analytical technique to generate a first output that is representative of the analyte content of the sample;
   (b) reacting a second aliquot of the sample in an enzyme-catalyzed or oxidative reaction that chemically changes the analyte in the second aliquot, wherein the reaction produces a product that is distinguishable from the analyte using the analytical technique;
   (c) analyzing the reacted second aliquot with the selected analytical technique to generate a second output that is representative of the analyte content of the reacted second aliquot and representive of the product content of the reacted second aliquot; and
   (d) comparing the two outputs to determine the presence or amount of analyte in the sample.

2. The method of claim 1 wherein the analytical technique is capillary electrophoresis.

3. A method for detecting an analyte in a sample, the method being suitable for samples containing compounds that can interfere with the detection of the analyte, the method consisting essentially of the following steps:
   (a) subjecting a first aliquot of the sample to capillary electrophoresis to generate a first electropherogram, wherein the first electropherogram is representative of the analyte content of the sample;
   (b) reacting a second aliquot of the sample in an enzyme-catalyzed or oxidative reaction that chemically changes the analyte in the second aliquot, wherein the reaction produces a product that is distinguishable from the analyte using capillary electrophoresis;
   (c) subjecting the reacted second aliquot to capillary electrophoresis to generate a second electropherogram, wherein the second electropherogram is representative of the analyte content of the reacted second aliquot and of the product content of the reacted second aliquot; and
   (d) comparing the first electropherogram with the second electropherogram to determine the presence or amount of analyte in the sample.

* * * * *